United States Patent
Burgo et al.

(10) Patent No.: US 10,709,650 B2
(45) Date of Patent: Jul. 14, 2020

(54) SPRAYABLE SUNSCREEN COMPOSITIONS AND METHODS

(71) Applicant: Inolex Investment Corporation, Wilmington, DE (US)

(72) Inventors: Rocco Burgo, Mullica Hill, NJ (US); Lorraine Lampe, West Chester, PA (US)

(73) Assignee: INOLEX INVESTMENT CORPORATION, Wilmington, DE (US)

( * ) Notice: Subject to any disclaimer, the term of this patent is extended or adjusted under 35 U.S.C. 154(b) by 0 days.

(21) Appl. No.: 14/671,782

(22) Filed: Mar. 27, 2015

(65) Prior Publication Data

US 2015/0272846 A1    Oct. 1, 2015

Related U.S. Application Data

(60) Provisional application No. 61/971,370, filed on Mar. 27, 2014.

(51) Int. Cl.

| | |
|---|---|
| *A61K 8/40* | (2006.01) |
| *A61Q 17/04* | (2006.01) |
| *A61K 8/33* | (2006.01) |
| *A61K 8/35* | (2006.01) |
| *A61K 8/34* | (2006.01) |
| *A61K 8/85* | (2006.01) |
| *A61K 8/31* | (2006.01) |
| *A61K 8/37* | (2006.01) |
| *A61K 8/86* | (2006.01) |

(52) U.S. Cl.
CPC ............... *A61K 8/40* (2013.01); *A61K 8/31* (2013.01); *A61K 8/33* (2013.01); *A61K 8/34* (2013.01); *A61K 8/345* (2013.01); *A61K 8/35* (2013.01); *A61K 8/375* (2013.01); *A61K 8/85* (2013.01); *A61K 8/86* (2013.01); *A61Q 17/04* (2013.01); *A61K 2800/31* (2013.01)

(58) Field of Classification Search
None
See application file for complete search history.

(56) References Cited

U.S. PATENT DOCUMENTS

| 5,989,527 A | * | 11/1999 | Siegfried | ............... A01N 25/24 |
| | | | | 424/409 |
| 2005/0048010 A1 | * | 3/2005 | Kliss | ...................... A61K 8/044 |
| | | | | 424/59 |

FOREIGN PATENT DOCUMENTS

| WO | WO 2012/149355 | * 11/2012 | ............... A61K 8/49 |

OTHER PUBLICATIONS

Lexorez 200, Product Bulletin, 2002.*

* cited by examiner

*Primary Examiner* — Brian Gulledge
(74) *Attorney, Agent, or Firm* — Cozen O'Connor

(57) ABSTRACT

Useful compositions are described herein that comprise a solvent base comprising at least one non-aqueous solvent; at least one sunscreen active ingredient that is a UV blocker and/or a UV absorber; and a polymer reaction product of a random polymerization of at least one organic diol, at least one polycarboxylic acid and at least one polyol having at least three functional groups. Such compositions are particularly useful in clear compositions including sunscreens for personal care including spray sunscreen formulations that are applied to and effective on wet skin, hair or nails.

21 Claims, 5 Drawing Sheets

SPRAYABLE SUNSCREEN COMPOSITIONS AND METHODS

CROSS-REFERENCE TO RELATED APPLICATIONS

This application claims the benefit under 35 U.S.C. § 119(e) of U.S. Provisional Patent Application No. 61/971,370, filed Mar. 27, 2014, entitled, "Sprayable Sunscreen Compositions and Methods," the entire disclosure of which is incorporated herein by reference.

BACKGROUND OF THE INVENTION

Field of the Invention

The invention relates to the field of sunscreen active personal care formulations, particularly those that are applied to mammal skin, hair or nails that are damp, moist or otherwise wet surfaces, and more particularly to sprayable sunscreen formulations.

Description of Related Art

The electromagnetic radiation (light energy) within the ultraviolet (UV) spectrum that reaches the earth's surface falls within the wavelength range of approximately 290 to 400 nanometers (nm). The portion of the spectrum that is responsible for erythema (sunburn) of skin is within the range of about 290 to 320 nm, and is referred to as UV-B. More recently, research has shown that not only sunlight energy within the UV-B range can be harmful to skin, but lower energy, longer wavelengths (known as UV-A) with a range of 320 to 400 nm may also be problematic. UV-C radiation (from about 200 to 290 nm) can also be problematic and is associated with artificial tanning, such as through sun lamps or tanning beds.

UV-A has been shown to penetrate the skin more deeply than UV-B. In studies which have occurred over the past two decades, it has been shown that the effects of prolonged UV-A exposure can result in premature skin aging, wrinkling, and has been implicated as a potential initiator for the development of skin cancers. UV-A damages skin cells in the basal layer of the epidermis (keratinocytes) where most skin cancers occur. In addition to harming skin, UV radiation can also cause damage to other areas, such as hair, causing it to change color and impacting color-treated hair as well, creating damage to the physical character of the hair and loss of shine or manageability.

Topical photoprotective treatments, such as sunscreens, have been developed to mitigate or prevent skin or hair damage. Sunscreen formulations are applied topically to protect against UV induced skin damage and are prepared in various forms, including creams, lotions, and sprays. Conventional sunscreen formulators will typically incorporate organic chemical compounds that chemically absorb UV radiation (organic UV filters) and inorganic compounds that in addition to absorbing, also physically scatter and/or reflect the radiation (UV blockers) into the sunscreen product.

For sunscreens to be used effectively, they need to be applied evenly and as directed. Misuse of sunscreens by improper or inconsistent application can result in grave problems. Ineffective application due to defects in the formulation's ability to be applied properly can be similarly problematic. Users may feel they are protected from the sun's rays and may take lesser steps to avoid exposure by physically covering the body by clothing or shade. Misapplication or under application can also result because the user may feel that the sunscreen product is aesthetically unpleasing or too greasy to the skin (blocking pores, etc.).

Historically, sunscreens were formulated predominantly to prevent sunburn and associated acute discomfort. Consequently, they included primarily UV-B filters and UV blockers. The ability of a given sunscreen to protect against sunburn is communicated to a consumer by use of the sun protection factor ("SPF") system. SPF is an in vivo laboratory measurement of the effectiveness of sunscreen in preventing sunburn. It is a numerical value. The higher the SPF, the more protection a sunscreen offers against UV-B. The SPF is further defined, and the detailed testing procedures are provided in United States Food and Drug Administration ("FDA") publication "Sunscreen Drug Products for Over-the-Counter Human Use"; Final Monograph; 21CFR Parts 310, 352, 700 and 740. Federal Register 64 (98) May 21, 1999. pp. 27666-27693, the contents of which are incorporated herein by reference.

Attempts have been made to develop sunscreens that include filters that also absorb UV-A radiation. In the U.S., the approved organic UV-A filter is limited to butyl methoxydibenzoylmethane (avobenzone or AVO) due to statutory requirements. AVO has been shown to degrade in the presence of sunlight by photolytic mechanisms, with the products of photodegradation being less effective at absorbing UV-A radiation than the parent compound. This means that protection against UV-A is reduced from time of initial application and upon subsequent exposure to sunlight when AVO is used as an UV-A filter. Photodegradation is particularly pronounced when AVO is used in combination with 2-ethylhexyl (2E)-3-(4-methoxyphenyl)prop-2-enoate (octylmethoxycinnamate, octinoxate, OMC.)

Regulatory activity has centered on the labeling of sunscreens and the development of better ways to convey to consumers a sunscreen's ability to not only protect against sunburn, but to also protect against UV-A damage. In 2007, the FDA published proposed amendments to the monograph for sunscreen drug products for over-the-counter human use. Within the amendments are revisions to the test-procedures for evaluating the efficacy of sunscreen products. In addition to SPF, the revisions include provisions for evaluating UV-A protection, as well as photostability. The FDA has also proposed a four-star UV-A protection rating system based on in vivo and in vitro testing methods. These values are further defined, and the detailed testing procedures are provided in, "U. S. Food and Drug Administration. Sunscreen Drug Products for Over-the-Counter Human Use"; Proposed Amendment of Final Monograph; Proposed Rule; 21CFR Parts 347 and 352. Federal Register 72 (165) Aug. 27, 2007. 49070-4912, the contents of which are incorporated herein by reference.

The European Cosmetics Association ("COLIPA") has also published guidelines and testing procedures relating to UV-A protection. In these documents, additional numerical parameters have been defined such as the in vitro SPF, and the in vitro UV-A protection factor. These parameters are further defined and the detailed testing procedures are provided in "Colipa Project Team IV, in-vitro Photoprotection Methods, Method for the in-vitro Determination of UVA Protection Provided by Sunscreen Products, Guideline, 2007", the contents of which are incorporated herein by reference.

Additional parameters have been defined, such as the UV-A/UV-B ratio, and the critical wavelength. The UV-A/UV-B ratio describes the performance of a sunscreen in the UV-A in relation to its performance in the UV-B range. It is calculated as the ratio between the areas under the UV-A and UV-B parts of the extinction curve, both areas being normalized to the range of wavelengths involved. The UV-A/UV-B ratio is further defined and detailed testing procedures are provided in "Measurement of UV-A/UV-B ratio according to the Boots Star rating system," (2008 revision), Boots UK Limited, Nottingham, NG2 3AA, UK (January 2008), the contents of which are incorporated herein by reference.

The critical wavelength is given as the upper limit of the spectral range from 290 nm on, within which 90% of the area under the extinction curve of the whole UV-range between 290 nm and 400 nm is covered. If that wavelength is 370 nm or greater, the product is considered "broad spectrum," which denotes balanced protection throughout the UV-B and UV-A ranges. The critical wavelength is further defined and detailed testing procedures are provided in Diffey B L, et al, "In-vitro assessment of the broad-spectrum ultraviolet protection of sunscreen products," J Amer Acad Dermatol 43:1024-35, 2000, the contents of which are incorporated herein by reference.

It has been discovered that certain sunscreen chemicals are absorbed across the skin and enter into systemic circulation. Particular attention has been given to the filter benzophenone-3.

With such guidelines in mind, most sunscreen formulators aspire to develop a sun care product that, when tested, obtains higher values for some or all of the numerical parameters described above, and thereby achieves an improvement over current sunscreen technology, and which includes polymeric filters to mitigate skin penetration. There remains also a need in the art for new ingredients, such as formulation ingredients and polymers, that can be used to better formulate photoprotective products so that properties such as photostability, pleasant aesthetics, higher SPF, and increased UV-A protection may be realized as well as optimized.

Sunscreens and other products having sunscreen protection, applicable to the skin, scalp, lips and/or hair while best applied before exposure, typically require re-application. They are applied as creams, lotions, or other cosmetic formulations (lip balm or liquid foundation for example). Most use is for exposure to the sun outdoors, for example, walking, participating in sports, running, swimming, beach activities, and the like. As noted above, while users do not generally like the use of a greasy formulation, creating a resistance to use, and there is a desire for a more "dry"—feeling formulation on application, it is also a problem when applied sunscreen products in whatever form are contacted with moisture—either from perspiration due to physical activity, from rain or from swimming, etc. The user also knows and desires (and good protection dictates) that if the product washes off, it will require re-application, which is difficult to do when wet, or can become greasy to the surface of the skin when wet, causing users to not re-apply either because they believe it will not be effective, because it feels oily or greasy or because it simply drips off or causes blotchy or spotty application on the skin.

Clearer formulations are preferred for use also by users, so that it does not appear they are wearing sunscreen when in use. If the sunscreen starts to smear, wipe off, drip or otherwise separate off the skin, it can appear white and/or clumped in oily-looking patches on the damp skin. This is not only an aesthetically undesirable result, it can discourage use and/or re-application when the skin becomes wet, leading to no protection and harm to the skin or hair.

The clear products are generally "anhydrous," meaning they have very little water in them and preferably less than about 5% water. Such formulations come in "clear" products like gels, clear lotions, or sprayable sunscreen products. In an anhydrous formulation, the active and inactive ingredients are generally in a solution form with a base solvent, such as an organic alcohol. Sprayable sunscreens based on alcohol solutions are a growing global product trend. The popularity of sprayable sunscreen formulations derives from their ease of use and application. When in an active setting, they take little time to apply, dry quickly and typically do not exhibit the greasiness associated with traditional sunscreen lotions and creams. In addition, they are easier to put on another person or yourself, which is especially useful for parents who need to apply sunscreen to themselves and to their children. In a beach situation, they are also less likely to have sand stuck in the lotion which is then rubbed into the skin.

A recent development increasing this popularity, especially for parents, is sprayable sport sunscreen products, which are intended to be sprayed directly onto wet skin, offer an advantage of more even coverage compared to traditional lotions and creams, and provide a more aesthetically pleasing look and feel. Further, when applied and working correctly, perform without a loss of efficacy in terms of broad spectrum sun protection and water resistance.

U.S. Pat. No. 8,778,313 B2 is directed to improving sunscreens for enhanced SPF and UV-A and UV-B protective sunscreens for spray use that incorporate at least one ester-terminated poly(ester amide) polymer in combination with a combined sunscreen protection system.

U.S. Patent Application Publication No. 2014/0017186 A1 is directed to a sprayable sunscreen formulation having a co-polymer formed from a vinyl monomer and an acid-functional monomer, with an optional different third vinyl monomer.

U.S. Patent Application Publication No. 2014/0348757 A1 discloses a sprayable alcohol-based sunscreen formulation using a film-forming polymer comprising shellac.

U.S. Patent Publication No. 2014/0170090 A1 teaches a sunscreen composition having avobenzone in an amount for providing UV-A protection, an alcohol, and an antioxidant such as a vitamin, and further may include a water-penetrating polymer which is hydrophobic such as an alkyl maleate/acrylate copolymer.

While it is important to continue to improve sunscreens in sprayable form that stay on the user better and provide desirable properties, those in the art are focusing on developing various combinations of sunscreen actives, or other additives as well as experimenting with different base polymers as noted in the patent and patent publications described above. However, there is still a need in the art for an improved formulation.

The applicant herein has provided film former technology into the sun care market for many years, including various polymers based upon variations in polyester technology, marketed under the Lexorez® brand. However, a need in the art still exists for vehicles and formulations to improve on the performance of clear anhydrous formulations, such as sprayable sunscreen formulations.

Alcohol-based spray sunscreens are typically simple solutions in ethanol of organic UV filters, emollients, and film formers. A major disadvantage of many existing sprayable sunscreens products in this area of the art is that when sprayed on wet skin, the oily components rapidly fall out of solution and coalesce. This then creates an aesthetically displeasing whitening due to the scattering of light at the phase interfaces. See FIG. 1.

Another negative result encountered is that a feeling of oiliness or greasiness on the skin surface is experienced due to coalesced filters and emollients. Consumers have historically demanded that sunscreens be as dry feeling as possible as noted above, and a sunscreen that feels greasy may be misused by under-applied. This results in insufficient protection against damaging UV rays.

Another negative aesthetic effect from such sprays is a residual shininess on the skin primarily caused by non-uniformity of the emollients and filters.

So as not to exhibit these deficiencies, an ideal sprayable or other clear-type anhydrous sunscreen should spread out quickly on the skin into a uniform film. Additionally, in sprayable formulations, the emollients and filters should not drop out of solution and coalesce.

There is a need in the art for solvent-based compositions, such as sprayable or other solvent-based sunscreen formulations, that eliminates the above-noted deficiencies in the art, and achieves a dry feel, an aesthetically pleasing appearance and feel on the skin and a uniform film application, particularly when the skin is exposed to wetness or moisture.

BRIEF SUMMARY OF THE INVENTION

The invention includes a composition, comprising: a solvent base comprising at least one non-aqueous solvent; at least one sunscreen active ingredient that is a UV blocker and/or a UV absorber; and a polymer reaction product of a random polymerization of at least one organic diol, at least one polycarboxylic acid and at least one polyol having at least three functional groups. In one preferred embodiment, it is also advantageous to include emollients such as esters in the compositions.

The at least one non-aqueous solvent may be an organic alcohol of about 1 to about 10 carbon atoms; an alkylene glycol; a polymeric alkylene glycol; a branched chain hydrocarbon of about 6 to about 22 carbon atoms; an alkyl ester or alkyl ether of an organic alcohol, an alkylene glycol, a branched chain hydrocarbon of about 6 to about 22 carbon atoms or a polymeric alkylene glycol; an alkyl ether or an alkyl ester; or a combination thereof. In one embodiment, the non-aqueous solvent is an organic alcohol selected from the group consistent of ethanol, propanol, isopropanol, butanol, isobutanol, pentanol, isopentanol and/or hexanol. In a further embodiment, the non-aqueous solvent is an alkylene glycol or a polymeric alkylene glycol selected from the group consisting of polypropylene glycol, polyethylene glycol and copolymers thereof; ethylene glycol; propylene glycol; butylene glycol; pentylene glycol; hexylene glycol; a diglycol; dodecane; isododecane or any of the branched chain hydrocarbons such as those available from ExxonMobil under the trade name Isopar™; and/or a diglycol. The non-aqueous solvent may also be dimethyl ether or a diethyl ether.

The solvent base may be present in an amount of at least about 35% to about 95% by weight of the composition, preferably wherein at least about 85% to about 100% of the solvent base is the non-aqueous solvent. More preferably, the solvent base may be present in the composition in an amount that is about 35% to about 65% of the composition, and wherein preferably at least about 95% to about 100% of the solvent base is the non-aqueous solvent.

In one embodiment, the at least one sunscreen active ingredient is present in an amount of about 0.5% to about 75% of the composition, more preferably about 5% to about 70% of the at least one sunscreen active ingredient is present in the composition, and most preferably about 20% to about 50% of the at least one sunscreen active ingredient is present in the composition.

The at least one sunscreen active ingredient may be selected from the group consisting of octocrylene, oxybenzone, octisalate, homosalate, avobenzone, octinoxate, and combinations thereof.

The polymer reaction product may be derived from the esterification of at least one organic diol, at least one polycarboxylic acid, and at least one polyol. The at least one organic diol may be 1,3-pentanediol, 2,2,4-trimethyl-1,3-pentanediol, 1,2-pentane diol, 2-methyl-1,3-propanediol and combinations thereof, and is most preferably 2,2,4-trimethyl-1,3-pentane diol.

The at least one polycarboxylic acid may be selected from the group consisting of propanedioic acid; decanedioic acid; pentanedioic acid; hexanedioic acid; heptanedioic acid; octanedioic acid; nonanedioic acid; and decanedioic acid, and combinations thereof. In one embodiment, the at least one polycarboxylic acid is a diacid, and is preferably hexanedioic acid The at least one polyol may be selected from the group consisting of dimerdiol, trimethylolpropane, ditrimethylolpropane, glycerol, 1,2,3-propane triol, and combinations thereof. The polymer is most preferably a random polymer of 2,2,4-trimethyl-1,3-pentane diol, heptanedioic acid and glycerol.

The invention further includes a method of preparing a sunscreen composition having a solvent base, comprising combining: (a) a non-aqueous solvent system; (b) a polyester polymer formed as an esterification reaction product of at least one polycarboxylic acid, at least one organic diol and at least one polyol; and (c) at least one sunscreen active ingredient that is a UV blocker and/or a UV absorber. In one embodiment, the non-aqueous solvent system comprises an alcohol of about 1 to about 10 carbon atoms and at least one branched chain hydrocarbon of about 6 to about 22 carbon atoms, wherein the at least one branched chain hydrocarbon may comprise an isoparaffin and/or an isoalkane.

The sunscreen active ingredient is preferably a UV absorber that is a UV filtering compound. The method may further comprises combining (d) at least one ester oil in the composition. In the method, the at least one branched chain hydrocarbon may comprise an isoparaffin and/or an isoalkane. The at least one polycarboxylic acid, at least one organic diol and at least one polyol are preferably reacted so as to have a ratio of organic diol:polycarboxylic acid:polyol of about 5:5:1 to about 25:25:1, and more preferably about 10:10:1. The esterification preferably occurs at about 100° C. to about 260° C. and at about 760 mm Hg to about 1 mm Hg.

The invention also includes in one embodiment thereof a composition suitable for use in a personal care formulation, comprising at least one sunscreen active ingredient that is a UV blocker and/or a UV absorber; and a polymer reaction product of a random polymerization of at least one polycarboxylic acid, at least one organic diol and at least one polyol, wherein a ratio of organic diol:polycarboxylic acid:polyol is about 5:5:1 to about 25:25:1.

Also within the scope of the invention hereof, is a method of increasing a sunscreen protection factor of a personal care formulation having at least one sunscreen active ingredient that is a UV blocker and/or a UV absorber, the method comprises providing to the personal care formulation a polyester polymer formed as an esterification reaction product of at least one polycarboxylic acid, at least one organic diol and at least one polyol. The personal care formulation may be a sprayable sunscreen and the formulation preferably comprises a non-aqueous solvent system. The non-aqueous solvent system in one preferred embodiment comprises an alcohol of about 1 to about 10 carbon atoms and at least one branched chain hydrocarbon of about 6 to about 22 carbon atoms, and may further comprises at least one ester oil in the composition. The at least one polycarboxylic acid, at least one organic diol and at least one polyol are preferably reacted so as to have a ratio of organic diol:polycarboxylic acid:polyol of about 5:5:1 to about 25:25:1, and more preferably about 10:10:1. In the method, the esterification occurs preferably at about 100° C. to about 260° C. and at about 760 mm Hg to about 1 mm Hg.

A further method is provided in the invention hereof, which is a method of increasing water resistance of a personal care formulation having at least one sunscreen active ingredient that is a UV blocker and/or a UV absorber, the method comprising providing to the personal care formulation a polyester polymer formed as an esterification reaction product of at least one polycarboxylic acid, at least one organic diol and at least one polyol. In the method, the personal care formulation may be a sprayable sunscreen and the formulation may comprise a non-aqueous solvent system, including one that preferably comprises an alcohol of about 1 to about 10 carbon atoms and at least one branched chain hydrocarbon of about 6 to about 22 carbon atoms. The formulation may further comprise at least one ester oil. The at least one polycarboxylic acid, at least one organic diol and at least one polyol are preferably reacted so as to have a ratio of organic diol:polycarboxylic acid:polyol of about 5:5:1 to about 25:25:1, and preferably about 10:10:1. The esterification preferably occurs at about 100° C. to about 260° C. and at about 760 mm Hg to about 1 mm Hg.

The invention also includes a method of reducing a whitening effect of a personal care formulation having at least one sunscreen active ingredient that is a UV blocker and/or a UV absorber when applied to wet skin, the method comprising providing to the personal care formulation a polyester polymer formed as an esterification reaction product of at least one polycarboxylic acid, at least one organic diol and at least one polyol. In the method, the personal care formulation may be a sprayable sunscreen and the formulation may comprise a non-aqueous solvent system, including one that preferably comprises an alcohol of about 1 to about 10 carbon atoms and at least one branched chain hydrocarbon of about 6 to about 22 carbon atoms. The formulation may further comprise at least one ester oil. The at least one polycarboxylic acid, at least one organic diol and at least one polyol are preferably reacted so as to have a ratio of organic diol:polycarboxylic acid:polyol of about 5:5:1 to about 25:25:1, and preferably about 10:10:1. The esterification preferably occurs at about 100° C. to about 260° C. and at about 760 mm Hg to about 1 mm Hg.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
FIG. 1 is an enlarged photographic representation of the appearance of whitening from a prior art sprayable sunscreen.
Figure 2:
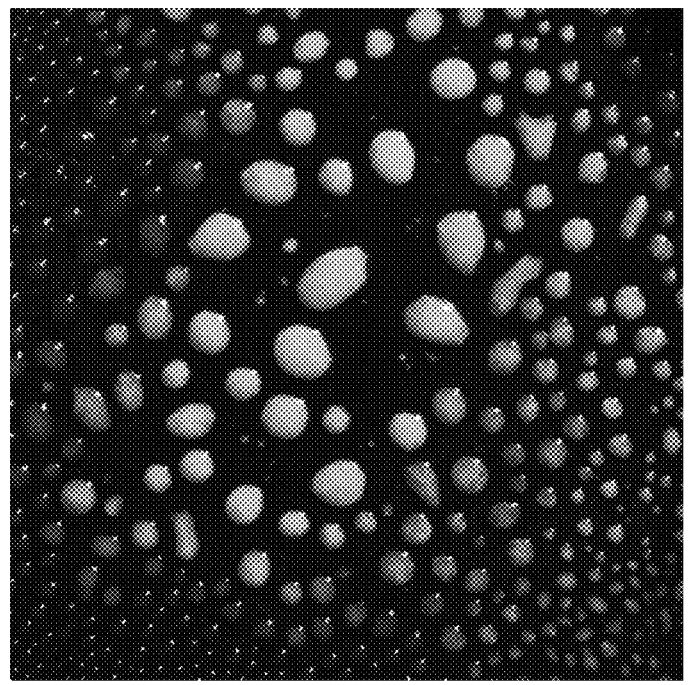
FIG. 2 is a photographic representation of a prior art sunscreen having oily component coalescence on skin.

The skin is a good barrier and is hydrophobic. As a result, water is not evenly dispersed when skin is wet. On wet skin, high local concentrations of water exist on the surface in the form of droplets. When using a sprayable-type sunscreen, when the sunscreen interacts with the water droplets, its composition is changed significantly. If the oily components (emollients, UV filters and polymers) of the sunscreen are very water intolerant, they are pushed out of the solution by the water and coalesce. "Water intolerant" herein refers to the rate and amount of coalescence that occurs when the sunscreen formulation comes in contact with the water. The coalescence results in a whitening effect due to the difference in refractive index between the oil and water phases. FIG. 1 shows a prior art wet-skin, alcohol-based spray sunscreen sprayed on wet skin. FIG. 2 shows a prior art wet-skin, alcohol-based spray sunscreen sprayed on 600 grit wet/dry sandpaper. These Figures illustrate this typical prior art sunscreen application effect.

Thus, applicants have determined that for an alcohol-based sunscreen to remain clear when sprayed on wet skin, water tolerance should be maximized. Applicants evaluated factors such as Hansen solubility parameters, density, and other similar properties to evaluate the effect of the inclusion of polyester film formers in sunscreen formulations to increase water tolerance.

As a result of this research, applicants have developed a formulation polymer that, among other things, significantly improves the water tolerance of alcohol-based formulations, including particularly spray sunscreen formulations, and also provides the benefit of excellent water resistance.

The compositions of the present invention are useful as sunscreen-containing products that have a dry feel and/or are substantially "clear" (meaning they are formulated for virtually no color when used on the skin) and/or are applied as a spray and/or employed in cosmetics having sunscreens, that minimize an aesthetically unappealing oily or greasy feel in use and which resist loss or separation of formulation components when applied on a wet keratinous surface such as skin or hair. They are especially suitable for, but not limited to, spray sunscreen formulations for use on wet human skin.

The compositions include at least one solvent, preferably a non-aqueous solvent; at least one sunscreen active ingredient that is a UV blocker and/or a UV absorber; and a polymer reaction product of a random polymerization of at least one organic diol, at least one dicarboxylic acid and at least one polyol having at least three functional groups. Such compositions may also include various optional cosmetic and/or sunscreen formulation components as are known in the art or to be developed as described further below.

As noted elsewhere herein, the compositions preferably are substantially anhydrous, but need not be fully non-aqueous solvent based, and so may include some water. Preferably, the composition has at least about 35% to about 95% of a solvent base, of which at least about 85% up to about 100% of the solvent base is a non-aqueous solvent. More preferably there is about 35% to about 65% of a solvent base, of which about 95% to about 100% is a non-aqueous solvent. While water is acceptable (preferably more than about 0 up to about 15%), in preferred embodiments, water is omitted or is only a minor component of the solvent base.

Suitable non-aqueous solvents include, but are not limited to organic alcohols, such as of about 1 to about 10 carbon atoms, including, but not limited to methanol, ethanol, propanol, isopropanol, butanol, isobutanol, pentanol, isopentanol, hexanol, and the like; polymeric glycols, such as polypropylene glycols or polyethylene glycols (PEGs) of varying length, and copolymers of such polymeric glycols, glycol compounds such as ethylene glycol, propylene glycol, butylene glycol, pentylene glycol, hexylene glycol, diglycols and similar compounds, sorbitols or isosorbitols; branched chain hydrocarbons of about 6 to about 22 carbon atoms, such as isoalkanes and isoparaffins of varying lengths (e.g., C10-13, C13-14, C13-16 isoparaffins or C8-13 or C9-12 isoalkanes) such as those available from ExxonMobil under the name Isopar™, isoolefins, isododecanes and the like; alkyl esters or alkyl ethers of any of the above alcohol, glycol or hydrocarbon compounds; volatile solvents such as ether solvents, for example, dimethyl ethers or diethyl ethers. Use of alcohols preferably includes of use denatured alcohol as commonly used in human skin care products and spray formulations.

The solvent base, including the non-aqueous solvent acts as a carrier compound for the sunscreen active agents and other components in the compositions herein.

In the composition, the at least one sunscreen active ingredient may be any acceptable a UV blocker and/or a UV absorber in whatever form that is useful in the desired sunscreen product preferably intended for initial use and/or re-application on skin having or subject to moisture, perspiration, water and the like, including but not limited to solvent-based or solvent/water-based lotions, cream, spray or other form of sunscreen products, cosmetics or hair care products having sunscreen in whatever form and similar products without intending to be limiting, even though the invention is especially useful in spray on sunscreen and hair products having sunscreens wherein the user has a skin or hair surface that is moist, damp, wet, etc. Such sunscreen actives can be an organic or inorganic compound, a UV-absorbing polymer, or the like. UV-absorbing polymers are disclosed, for example, in applicant's co-pending U.S. Publication No. 2011/0104078 A1, incorporated herein, in relevant part, by reference.

Other suitable UV blocking and/or absorbing materials include but are not limited to non-polymeric chemical UV filters, such as, octyl triazone, diethylhexyl butamido triazone, diethylamino hydroxybenzoyl hexyl benzoate, isotrizinol, dimethico-diethylbenzalmalonate, polysilicone-15, isopentenyl-4-methoxycinnamate, ethylhexyl methoxycinnamate, ethylhexyl triazone, p-aminobenzoic acid (PABA), octyldimethyl-PABA, PEG-25 PABA, ethylhexyl dimethyl PABA, methylene bis-benztriazolyl tetramethylbutylphenol, bisodium phenyl dibenzimidazole tetrasulfonate, bis-ethylhexyloxyphenol methoxyphenol triazine, phenylbenzimidazole sulfonic acid, 2-ethoxyethyl p-methoxycinnamate, benzophenone-8, benzophenone-5, benzophenone-4, benzophenone-3, homomethyl salicylate, meradimate, octocrylene, octyl methoxycinnamate, isoamyl p-methoxycinnamate, oxybenzone, octisalate, homosalate, avobenzone, octinoxate, octyl salicylate, sulisobenzone, trolamine salicylate, avobenzone, terephthalylidene dicamphor sulfonic acid, camphor benzalkonium methosulfate, phenylbenzimidazole sulfonic acid, 4-methylbenzylidene camphor, terephthalidene dicamphor sulfonic acid, benzylidene camphor sulfonic acid, polyacrylamidomethyl benzylidene camphor, 4-methylbenzylidene camphor, 3-benzylidene camphor, ethylhexyl salicylate, bisoctrizole, bis-ethylhexyloxyphenol methoxyphenol triazine, bisdisulizole disodium, drometrizole trisiloxane, polysilicone-15, sodium dihydroxy dimethoxy disulfobenzophenone, ethylhexyl triazone, diethylamino hydroxybenzoyl hexyl benzoate, diethylhexyl butamido triazone, dimethico-diethylbenzalmalonate, drometrizole trisiloxane, as well as UV blockers such as titanium dioxide, silicone-treated titanium dioxides, zirconium oxides, zinc oxide, talc, cerium oxides, chromium oxides, cobalt oxides, iron oxides, red petrolatum, and combinations of these materials (filters/absorbers or blockers) together or with others as are known or to be developed in the art.

Typically, such materials are used in combinations useful for effect or synergy to achieve desired blocking or absorbing combinations. The invention is more directed to maintaining such materials and other additives in the compositions, however, and so it is not intended that the sunscreen active ingredient(s) used are limited.

The sunscreen active agent(s) is/are preferably present in an amount effective to provide sunscreen protection consistent with the desired SPF of the composition and can be from about 0.5% to about 75% of the composition, preferably about 5% to about 70% of the composition, and most preferably about 20% to about 50% of the composition, although the amount may be adjusted for desired end effects and based on the selected active ingredients as is known in the art.

The a novel polymers used in the compositions herein are preferably one or more reaction products of random polymerization of at least one organic diol, at least one dicarboxylic acid and at least one polyol having at least three functional groups, and are preferably reaction products derived from the esterification of at least one organic diol, at least one polycarboxylic acid and at least one polyol. Such polymers typically form polyesters or polyether polyols which are cross-polymers, i.e., they are cross-linked polymer chains having a cross-link density of about 0.1 to about 2.0. The cross-linking may be controlled by adjusting the amount of polyol in the monomer charge to the reaction.

Suitable organic diols are one or more such diols which may be branched and/or linear, saturated and/or unsaturated, aliphatic and/or aromatic and are about two to about fifty four carbon atoms in length with two hydroxyl groups, including, for example, ethylene glycol, 2,2,4-trimethyl-1-3 pentane diol, 1,2-propanediol; 1,3-propanediol; 1,3-butylene glycol; 1,4-butanediol; 2-methyl-1,3-propanediol; diethylene glycol; tetraethylene glycol; 1,5-pentanediol;

neopentyl glycol; 1,6-hexanediol; dipropylene glycol; 1,2-octanediol; dimerdiol, and combinations of the above components. Preferred compounds are pentane diols and alkyl pentane diols.

The at least one polycarboxylic acid may be an acid or in its anhydride form, but is preferably an acid for random polymerization. Further, while polyacids having more than two carboxylic acid groups (or their anhydride forms) may be used, a diacid is preferred. Suitable polyacids may be branched and/or linear, saturated and/or unsaturated, aliphatic and/or aromatic and may have from about two to about fifty four carbon atoms, and two to four, but more preferably two, carboxylic acid and/or anhydride groups, specifically preferred are diacids. Such acids may also have from zero to two sulfonic acid groups (and acid salts thereof). Examples of preferred polyacids are without limitation, carbonic acid; propanedioic acid; decanedioic acid; pentanedioic acid; hexanedioic acid (adipic acid); heptanedioic acid; octanedioic acid; nonanedioic acid; decanedioic acid; dimer acid; trimer acid; tetramer acid; phthalic acid; isophthalic acid; pyromellitic acid; naphthylene dicarboxylic acid; sodium sulfophthalic acid and combinations thereof.

The above-noted polyacids and/or organic diols may omit any UV-absorbing moiety or may contain an UV-absorbing entity as described in U.S. Publication No. 2011/0104078 A1.

The polyols are preferably those which have three or more hydroxyl groups to provide a site of cross-linking as well as reactive functionality. Suitable polyols include but are not limited to dimerdiol, trimethylolpropane, ditrimethylolpropane, glycerol, 1,2,3-propane triol, and combinations thereof. Preferably, the polyol is glycerol.

The random polymer is preferably combined in a manner that the ratio of diol:polycarboxylic acid:polyol is about 5:5:1 to about 25:25:1, and most preferably about 10:10:1. The polymer is preferably formed by thermal esterification at from about 100° C. to about 250° C. and a pressure of about 760 mmHg to about 1 mm Hg.

Other components may be provided to the composition including those known in the art of sunscreen formulations, or for use in personal care compositions such as cosmetics the require a sunscreen. Particularly preferred are emollients, such as esters. The compositions may include, optionally, for example, surfactants, buffers, perfumes, colorants, dyes, viscosity modifiers, water, oils, emulsifiers, preservatives, antioxidants, emollients, thickeners, gellants, vitamins, humectants, alcohols, botanical extracts and powders. Other suitable additive or components include may include one or more vegetable oils in the product, such as, for example, almond oil, castor oil, coconut oil, corn (maize) oil, cottonseed oil, canola oil, flax seed oil, hempseed oil, nut oil, olive oil, palm oil, peanut oil, safflower oil, sesame oil, soybean oil, sunflower oil, jojoba oil and combinations of these oils.

Surfactants may be included in the personal care composition, such as, for example, an anionic surfactant, a zwitterionic surfactant, a cationic surfactant, a non-ionic surfactant and combinations of these. Other exemplary components or additives may include, without limitation, lipids, additional alcohols, waxes, pigments, vitamins, fragrances, bleaching agents, antibacterial agents, anti-inflammatory agents, antimycotic agents, thickeners, gums, starches, chitosan, polymeric materials, cellulosic materials, glycerin, proteins, amino acids, keratin fibers, fatty acids, siloxanes, botanical extracts, abrasives and/or exfoliants (chemical or mechanical), anticaking agents, antioxidant agents, binders, biological additives, buffering agents, bulking agents, chelating agents, chemical additives, denaturants, external analgesics, film formers, humectants, opacifying agents, pH adjusters, preservatives, propellants, reducing agents, sunscreen agents, skin darkening agents, essential oils, skin sensates, and combinations of these.

The personal care composition of the invention may also include one or more optical brighteners as described in U.S. Patent Publication No. 2011/0104078 A1, incorporated in relevant part herein by reference, and also including for example, a triazine-stilbenes (di-, tetra- or hexa-sulfonated), a courmarin, an imidazoline, a diazole, a triazole, a benzoxazoline, and a biphenyl stilbene.

Also included within the scope of the invention is a method of protecting skin, hair, and/or nails of a mammal from damage caused by exposure to light in the UV wavelengths by applying to the skin, hair or nails a composition as described above, and that is particularly useful when the skin, hair or nails is damp, moist or otherwise wet. "Skin" includes the external integument of living mammals, reptiles, amphibians, birds and other animals as well as processed skins, such as leathers or suedes. "Hair" includes hair, fur, wool and other filamentous keratinized structures of mammals and other animals. Similarly, "nails" includes claws, hooves and analogous structures of mammals and other animals.

Also within the scope of the invention are methods to improve the aesthetics of photoprotective formulations by using the composition so as to avoid a feeling of oiliness and/or greasiness without substantial loss or separation of ingredients when skin is damp, moist or otherwise wet.

The invention will now be described with respect to the following non-limiting examples:

Example 1

In this example, Phase A ingredients, identified in Table 1 below, were heated to 40° C. or until the solids were dissolved, and mixed until uniform.

The Phase B ingredients from Table 1 were mixed until uniform.

Figure 3:
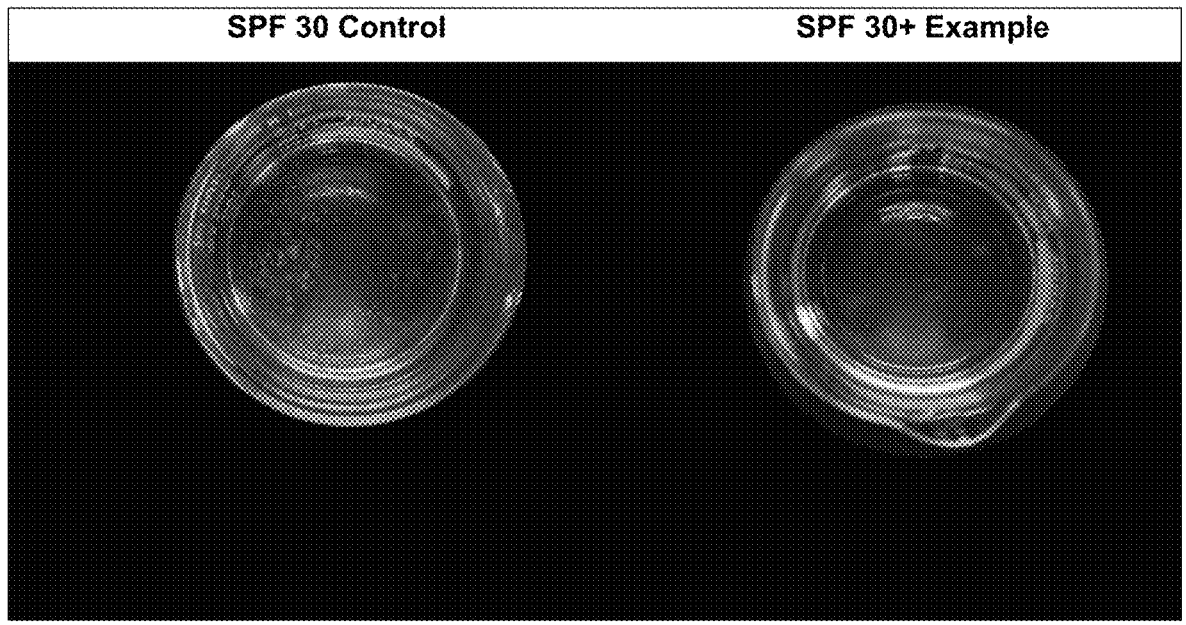
FIG. 3 is a photographic representation of a Control and Inventive Example after the test described in Example 1.

The uniform Phase B ingredients were added to the Phase A ingredients after the Phase A Ingredient mixture had cooled to room temperature and all ingredients were mixed well to form sunscreen formulations As a screening tool, the applicant herein developed a simple water dispersibility test. In the test, 0.1 gram of a sunscreen formulation was dropped into 100 grams of deionized water in a 200 milliliter beaker. This simulates the extreme dilution that occurs when fine atomized droplets of sunscreen lay upon large water droplets on the skin. FIG. 3 shows a comparison of the Control formulation versus the Example formulation containing a polymer according to the invention herein. The photos in FIG. 3 show clearly how the addition of only the inventive polymer to the Example formulation dramatically improved the water tolerance and dispersibility of the oil phase components in dilute solution in water, which is the key to non-whitening efficacy prior to rubbing in of the product.

TABLE 1

| Ingredients | Trade Name | SPF 30 Control | SPF 30+ Example |
|---|---|---|---|
| Phase A | | | |
| Neopentylglycol Diheptanoate (and) Propylene Glycol Dibenzoate | LexSolv ™ A [1] | 4.00 | 4.00 |
| Trimethyl-pentanediol/Adipic Acid/Glycerin Crosspolymer | Example Polymer | — | 2.00 |
| Octocrylene | NeoHeliopan 303 [2] | 2.75 | 2.75 |
| Oxybenzone | NeoHeliopan BB [2] | 6.00 | 6.00 |
| Octisalate | NeoHeliopan 303 [2] | 5.00 | 5.00 |
| Homosalate | NeoHeliopan HMS [2] | 10.00 | 10.00 |
| Avobenzone | NeoHeliopan 357 [2] | 3.00 | 3.00 |
| Octinoxate | NeoHeliopan AV [2] | 7.50 | 7.50 |
| Phase B | | | |
| Alcohol SDA 40B | SD Alcohol 40B | 57.25 | 55.25 |
| C9-12 Isoalkanes | Isopar H Fluid [3] | 1.00 | 1.00 |
| C13-14 Isoparaffin | Isopar M Solvent [3] | 3.50 | 3.50 |
| Total | | 100.00 | 100.00 |

[1] Available from Inolex, Inc., Philadelphia, PA;
[2] Available from Symrise AG, Teterboro, NJ; and
[3] Available from ExxonMobil, Houston, TX.

To further illustrate the improvement conferred by the inventive example formulation over the control, the SPF 30 Control and SPF-30+ inventive Example formulations were sprayed onto wet, 600-grit, black sandpaper in an identical manner. While sandpaper is not a substitute for human skin, the results clearly showed similar behavior to that which was experienced in vivo, but was much easier to see in photographic form.

Figure 4:
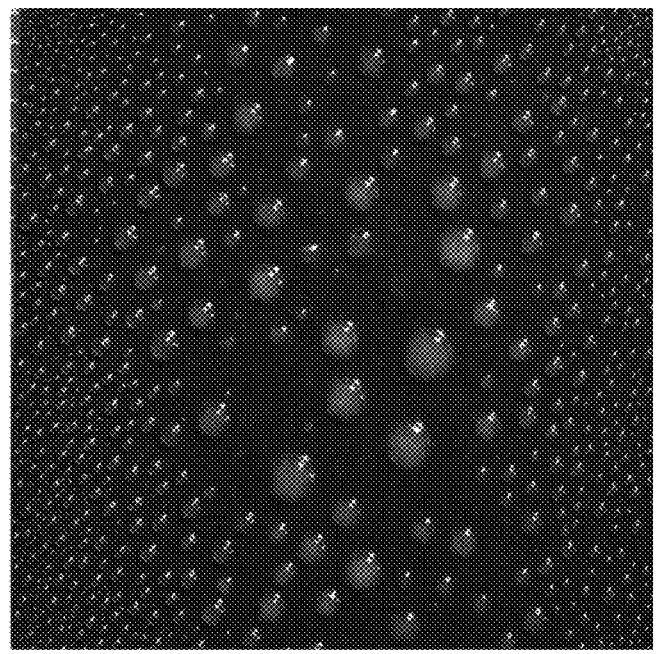
FIG. 4 is a photographic representation of the Control formulation of Example 1 on sandpaper.
Figure 5:
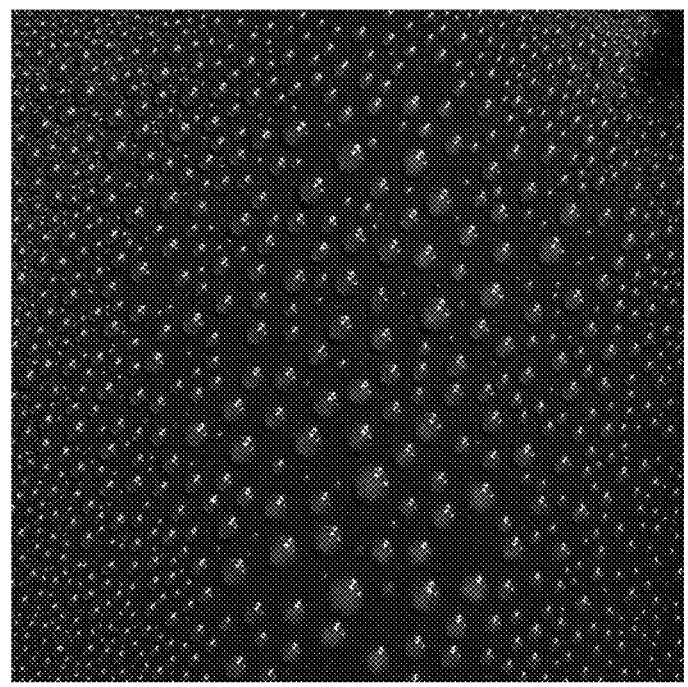
FIG. 5 is a photographic representation of the inventive Example formulation of Example 1 on sandpaper.

FIG. 4 shows the Control formulation. It is clear by the larger droplet size and whitening within the droplets that coalescence and plating out of the oily components has occurred. FIG. 5 illustrates how the addition of the inventive Example polymer has reduced coalescence, and virtually eliminated any whitening effect.

Figure 6:
FIG. 6 is a photographic representation of the Control formulation of Example 1 on human skin.
Figure 7:
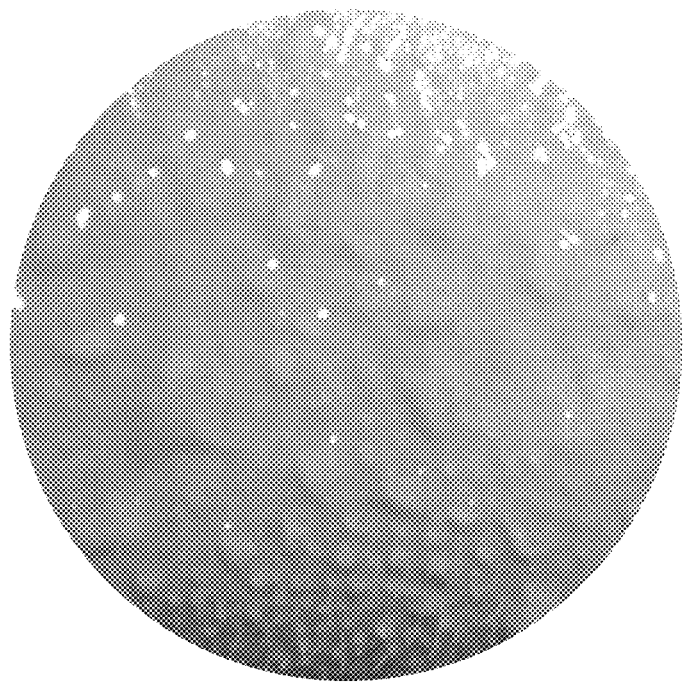
FIG. 7 is a photographic representation of the inventive Example formulation of Example 1 on human skin.

FIGS. 6 and 7 show the comparison of the two formulations on human skin.

Example 2

Using the formulations of Example 1, further evaluations were undertaken to measure various parameters of the formulations.

In-vivo Whitening and Gloss After Drying:

Whitening:

The Minolta Chroma Meter CR-300 is a useful tool for the objective assessment of surface color, and is often used in studies to quantify skin color change. Typical applications where it has been used is in the determination of the efficacy of anti-irritants, tanning accelerators, and antiperspirants. It is a reflectance colorimeter, and surface color data is output in the form of the L*a*b* color coordinate system. The L* value relates to skin lightness, while the a* (red/green) and b* (blue/yellow) values are measures of skin color. Since the base color of individual subjects varies, it is important to use a combination of the L*, a* and b* coordinates to determine changes before and after application of any product that is expected to change the color of the skin. The value that represents the complete picture, ΔE* is a linear combination of the changes in both skin lightness as well as color. ΔE* is calculated using the following equation:

$$\Delta E^* = \sqrt{(\Delta L^*)^2 + (\Delta a^*)^2 + (\Delta b^*)^2}$$

wherein ΔL*, Δa*, and Δb* are differences between values obtained before and after product application. The lower change in ΔE* change, the less the color of the skin is altered.

Figure 8:
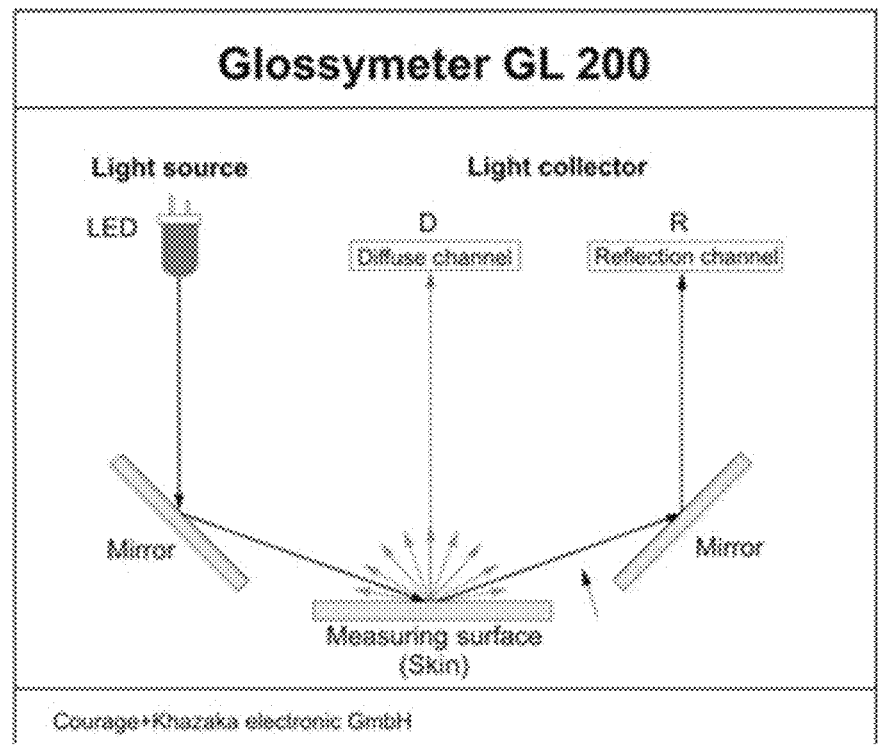
FIG. 8 is a schematic representation illustrating the operation of a Skin Glossymeter used in Example 2.

Shine:

The gloss of the surface of skin can be expressed by direct reflection of light sent to the surface. The Skin-Glossymeter GL-200, from Khazaka of Köln is a probe which measures both the portion of directly reflected light (Reflection channel, R) which is related to the gloss, and the scattered portion from the surface (Diffuse channel, D) as illustrated in the schematic representation of FIG. 8 provided by Khazaka. The value obtained, the Skin Gloss Value (SGV) is unitless, and is a function of probe design. Additionally, the Skin-Glossymeter GL-200 is specially designed to assess the gloss of the skin surface with diffuse scattering correction (DSC), thus allowing the comparison of gloss measurements obtained from different skin types accurately without interference of skin color or formulation color.

Procedure

Volunteers were allowed acclimate with the environment by waiting in a controlled setting of 22-24° C., at 15-20% relative humidity for 20 minutes. Areas of the volar forearm were cleaned with isopropanol and wiped dry with a paper towel prior to being marked with four centimeter diameter circles sufficient for control and treatment application of the product. Control color index values L*, a* and b* were then obtained. Test areas were then sprayed with 0.3 grams of water, then evenly sprayed with 0.3 grams of the sunscreen. Subjects were then held in the waiting area for twenty minutes over which time the sunscreens completely dried. Control color index values L*, a* and b* were again obtained.

In addition to the above, visual observations were made using a rating system from 0-10 with a higher value relating to higher whitening.

Figure 9:
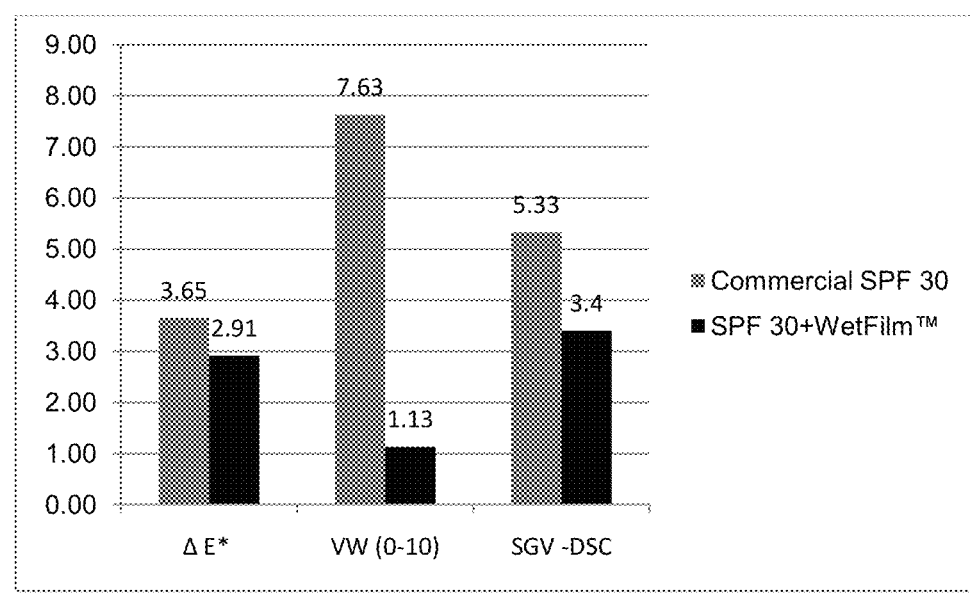
FIG. 9 is a graphical representation of a comparison of properties described in Example 2 using an existing spray sunscreen formulation for wet skin and the Inventive Example from Example 1 in side-by-side comparison tests on human subjects.

Lastly, skin gloss values were obtained using the Glossymeter GL-200. The above information was obtained for the SPF 30+inventive Example formulation to compare it with a current leading commercial alcohol spray formulation designed for wet skin including in its formulation in active part: 3% avobenzone, 8% homosalate, 4% octisalate, 8% octocrylene, 5% oxybenzone and various inactive ingredients (denatured alcohol, dimethyl ether, octyldodecyl citrate crosspolymer, acrylates/octylacrylamide copolymer, ethyl methicone, cetyl dimethicone, dimethicone, acrylates/dimethicone copolymer, fragrance, tocopheryl acetate, vinyl dimethicone crosspolymer, nelumbo nucifera flower powder, diethylhexyl-2,6-naphthalate, ascorbyl palmitate and retinyl palmitate). The results are shown graphically in FIG. 9.

Example 3

In the Example, static SPF value and water resistance SPF were obtained through clinical testing on the skin of panelists. ISO Standard 24444, incorporated herein by reference, was used to evaluate in-vivo SPF and water resistance on dry skin. A modification of ISO 24444 in which static SPF and water resistance was measured on wet skin was also employed. The modification consisted of pre-spraying the skin with 2 mg/cm² of water immediately before applying the sunscreen. The formulation is shown in Table 2 below as Formulation A.

TABLE 2

| Ingredients (% wt/wt) | Trade Name | Formulation A |
|---|---|---|
| Neopentylglycol Diheptanoate (and Propylene Glycol Dibenzoate | LexSolv ™[1] | 5.00 |
| Trimethyl-pentanediol/Adipic Acid/Glycerin Crosspolymer | Example 2 Polymer | 2.00 |
| Octocrylene | NeoHeliopan 303[2] | 10.00 |
| Bis-Ethylhexyloxyphenol | Tinosorb S[3] | 3.00 |
| Octisalate | NeoHeliopan OS[2] | 5.00 |
| Diethylamino Hydroxybenzoyl Hexyl Benzoate | Unival A+[3] | 2.00 |
| Ethylhexyl Triazone | Unival T-150[3] | 3.00 |
| Homosalate | NeoHeliopan HMS[2] | 10.00 |
| Avobenzone | NeoHeliopan 357 | 3.00 |
| Alcohol SDA 40B | — | 52.50 |
| Isododecane | Permethyl 99A[4] | 4.50 |
| Total | | 100.00 |

[1]Inolex, Inc.
[2]Symrise
[3]BASF
[4]Presperse

The results are shown below in Table 3, wherein static SPF and Water Resistance values represent an average of the three subject data:

TABLE 3

| Sunscreen Formulation | Static SPF (Dry Skin) | Water Resistance SPF (80 min., Dry Skin) | Static SPF (Wet Skin) | Water Resistance SPF (40 min., Wet Skin) |
|---|---|---|---|---|
| A | 56 | 52 | 56 | 52 |

The data support that the formulation has equivalent SPF when applied to both dry and wet skin, and is water resistant when applied to both dry and wet skin.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A composition, comprising:
   a solvent base comprising at least one non-aqueous solvent;
   at least one sunscreen active ingredient that is a UV blocker and/or a UV absorber; and
   a polymer that is a reaction product of a random polymerization of at least one organic diol, at least one polycarboxylic acid and at least one polyol having at least three functional groups, wherein a ratio of the at least one organic diol to the polycarboxylic acid to the polyol is about 5:5:1 to about 25:25:1 and wherein the polymer reduces a whitening effect of the composition on wet skin in comparison to a composition with the same components but without the polymer.

2. The composition according to claim 1, wherein the at least one non-aqueous solvent is an organic alcohol of about 1 to about 10 carbon atoms; an alkylene glycol; a polymeric alkylene glycol; a branched chain hydrocarbon of about 6 to about 22 carbon atoms; an alkyl ester or alkyl ether of an organic alcohol, an alkylene glycol, a branched chain hydrocarbon of about 6 to about 22 carbon atoms or a polymeric alkylene glycol; an alkyl ether or an alkyl ester; or combinations thereof.

3. The composition according to claim 2, wherein the non-aqueous solvent comprises ethanol and/or a branched chain hydrocarbon of about 6 to about 22 carbon atoms.

4. The composition according to claim 2, wherein the non-aqueous solvent is an alkylene glycol or a polymeric alkylene glycol selected from the group consisting of polypropylene glycol, polyethylene glycol and copolymers thereof; ethylene glycol; propylene glycol; butylene glycol; pentylene glycol; hexylene glycol; a diglycol; dodecane; a branched chain hydrocarbon of about 1 to about 22 carbon atoms.

5. The composition according to claim 2, wherein the non-aqueous solvent is a dimethyl ether or a diethyl ether.

6. The composition according to claim 1, wherein solvent base is at least about 35% to about 95% by weight of the composition.

7. The composition according to claim 6, wherein at least about 85% to about 100% of the solvent base is the non-aqueous solvent.

8. The composition according to claim 6, wherein the solvent base is about 35% to about 65% of the composition.

9. The composition according to claim 8, wherein at least about 95% to about 100% of the solvent base is the non-aqueous solvent.

10. The composition according to claim 1, wherein the composition comprises about 0.5% to about 75% of the at least one sunscreen active ingredient.

11. The composition according to claim 10, wherein the composition comprises about 5% to about 70% of the at least one sunscreen active ingredient.

12. The composition according to claim 11, wherein the composition comprises about 20% to about 50% of the at least one sunscreen active ingredient.

13. The composition according to claim 1, wherein the at least one sunscreen active ingredient is selected from the group consisting of octocrylene, oxybenzone, octisalate, homosalate, avobenzone, octinoxate, and combinations thereof.

14. The composition according to claim 1, wherein the at least one organic diol is 1,3-pentanediol, 2,2,4-trimethyl-1,3-pentanediol, 1,2-pentane diol, 2-methyl-1,3-propanediol and combinations thereof.

15. The composition according to claim 14, wherein the at last one organic diol is 2,2,4-trimethyl-1,3-pentane diol.

16. The composition according to claim 1, wherein the at least one polycarboxylic acid is selected from the group consisting of propanedioic acid; decanedioic acid; pentanedioic acid; hexanedioic acid; heptanedioic acid; octanedioic acid; nonanedioic acid; and decanedioic acid.

17. The composition according to claim 16, wherein the at least one polycarboxylic acid is a diacid.

18. The composition according to claim 17, wherein the at least one polycarboxylic acid is hexanedioic acid.

19. The composition according to claim 1, wherein the at least one polyol is selected from the group consisting of dimerdiol, trimethylolpropane, ditrimethylolpropane, glycerol, 1,2,3-propane triol, and combinations thereof.

20. The composition according to claim 1, wherein the polymer is a random polymer of 2,2,4-trimethyl-1,3-pentane diol, heptanedioic acid and glycerol.

21. A composition suitable for use in a personal care formulation, comprising at least one sunscreen active ingredient that is a UV blocker and/or a UV absorber; and a polymer that is a reaction product of a random polymerization of at least one polycarboxylic acid, at least one organic diol and at least one polyol, wherein a ratio of the at least one organic diol:polycarboxylic acid:polyol is about 5:5:1 to about 25:25:1 and wherein the polymer reduces a whitening effect of the formulation on wet skin in comparison to a formulation with the same components but without the polymer.

* * * * *